United States Patent [19]

Lynd et al.

[11] Patent Number: 5,258,293
[45] Date of Patent: Nov. 2, 1993

[54] CONTINUOUS PROCESS FOR ETHANOL PRODUCTION FROM LIGNOCELLULOSIC MATERIALS WITHOUT MECHANICAL AGITATION

[75] Inventors: Lee R. Lynd, Meriden, N.H.; David A. Hogsett, Fairlee, Vt.; Gisbert Spieles, Cologne, Fed. Rep. of Germany

[73] Assignee: Trustees of Dartmouth College, Hanover, N.H.

[21] Appl. No.: 695,516

[22] Filed: May 3, 1991

[51] Int. Cl.$^5$ ............................................. C12P 7/10
[52] U.S. Cl. ................................ 435/165; 435/163; 435/161; 435/162; 435/813
[58] Field of Search ............... 435/162, 161, 163, 165, 435/813; 426/14

[56] References Cited

U.S. PATENT DOCUMENTS

| | | | |
|---|---|---|---|
| 2,440,925 | 5/1948 | Boeckeler | 435/162 |
| 2,450,218 | 9/1948 | Victorero | 435/813 |
| 2,451,156 | 10/1948 | de Mattos | 435/162 |
| 3,413,124 | 11/1968 | Akin | 435/813 |
| 4,009,075 | 2/1977 | Hoge | 435/162 |
| 4,346,113 | 8/1982 | Faust et al. | 426/12 |
| 4,349,628 | 9/1982 | English et al. | 435/161 |
| 4,376,163 | 3/1983 | Ehnstrom | 435/162 |
| 4,413,058 | 11/1983 | Arcuri et al. | 435/813 |
| 4,443,544 | 4/1984 | Rogers et al. | 435/813 |
| 4,447,534 | 5/1984 | Moebus et al. | 435/161 |
| 4,460,687 | 7/1984 | Ehnström | 435/162 |
| 4,568,644 | 2/1986 | Wang et al. | 435/161 |
| 4,876,196 | 10/1989 | Salzbrunn et al. | 435/162 |
| 4,886,751 | 12/1989 | Thorson | 435/162 |
| 4,889,805 | 12/1989 | Da Silva Telles et al. | 435/813 |
| 4,952,503 | 8/1990 | Granstedt | 435/162 |

FOREIGN PATENT DOCUMENTS

WO83/01627 5/1983 PCT Int'l Appl.

OTHER PUBLICATIONS

Andrews, G., Biotechnology and Genetic Engineering Reviews, vol. 6, pp. 151-178 Sep., 1988.
Andrews, G., Biotechnol. Prog. 1990, 6, 225-230.
Kleijntjens, R. H., et al. Biotechnology Letters, vol. 8, No. 9, pp. 667-672 (1986).
Liu, Hwai-Shen, et al., Biotechnology Progress, vol. 4, No. 1, 40-46 (1988).
Lynd, L. R., et al., Applied and Environmental Microbiology, vol. 55, No. 12, 3131-3139 (1989).
Lynd, L. R., Advances in Biochemical Engineering Biotechnology, vol. 38, (1989).
Wright, J. D., Chemical Engineering Progress, pp. 62-64, (1988).
Zertuche et al., "A Study of Producing Ethanol from Cellulose Using *Clostridium thermocellus*," Biotechnol Bioengineering, 24 pp. 57-68, 1982.
Mistry et al., "Production of Ethanol by *Clostridium thermosaccharolyticium*: I Effect of Cell Recycloand Environmental Parmenters", Biotechnol Bioengineering vol. 34, pp. 1295-1304, 1989.
Ghose et al., "Simultaneous Saccharification and Fermentation (SSF) of Lignicellulosics to Ethanol Under Vacuum Cycloxy and Step Feeding", Biotechnol Bioengineering, vol. 26, pp. 377-381 1984.

Primary Examiner—Marian C. Knode
Attorney, Agent, or Firm—Lahive & Cockfield

[57] ABSTRACT

An improved and highly productive method of continuously producing ethanol from lignocellulosic substrates is provided. The method involves providing a suitable microbial system within a reaction vessel and adding fermentable substrate to the reactor to form a reaction mixture. The fermentation reaction is allowed to proceed while a quiescent state is maintained within the reactor. During the fermentation, soluble substrate is differentially retained relative to the feed slurry and reaction biocatalysts are retained and internally recycled within the system. Further, while fermenting substrate is retained within the system, it forms a stratified zone within the reactor such that the concentration of actively fermenting substrate is highest at upper portions of the reaction zone and is lowest, near zero, at a lower portion of the reaction zone. Insoluble, fully reacted substrate may be withdrawn from a region near the bottom of the reactor.

13 Claims, 1 Drawing Sheet

CONTINUOUS PROCESS FOR ETHANOL PRODUCTION FROM LIGNOCELLULOSIC MATERIALS WITHOUT MECHANICAL AGITATION

BACKGROUND OF THE INVENTION

The present invention relates to a method for producing ethanol from lignocellulose-containing raw materials.

Among the process options for producing ethanol from lignocellulosic substrates (e.g., trees, grasses, and solid wastes) are those known as Direct Microbial Conversion ("DMC") and Simultaneous Saccharification and Fermentation ("SSF"). In the DMC method, a single microbial system both produces cellulase enzyme and produces ethanol as a fermentation product. The SSF method utilizes two microbial systems, one of which produces cellulase enzyme and the other of which carries out the fermentation process to produce ethanol.

Biologically-mediated process steps are the most costly and the least developed in current designs for ethanol production. Typical ethanol production methods for lignocellulosic substrates require very long reaction times (e.g., about one week), and hence the bioreactors used in the process must have very large volumes for a given rate of throughput. As a result the bioreactor in which solids conversion takes place is a key cost component.

Accordingly, there is a need for a method of producing ethanol from cellulosic substrates using bioreactors characterized by higher volumetric productivity (rate of throughput per unit volume), and at a lower production cost.

It is thus an object of the invention to provide a method of producing ethanol from lignocellulosic substrates in an economically feasible manner. A further object of the invention is to provide a bioreactor suitable for carrying out such a method of producing ethanol from lignocellulosic substrates. Another object of the invention is to provide a bioreactor for the production of ethanol from organic substrates which possesses a high volumetric productivity. It is also an object of the invention to provide a method, and a suitable bioreactor, useful for the large-scale production of ethanol from lignocellulosic substrates. Other objects of the invention will be apparent to those of ordinary skill in the art upon reading the disclosure which follows.

SUMMARY OF THE INVENTION

The invention is directed to a method of producing ethanol from lignocellulose-containing raw materials, and a bioreactor which is suitable for carrying out the ethanol production process. The method is applicable to both the DMC and SSF process options.

According to the invention, the process commences by placing a feed slurry of fermentable, lignocellulosic substrate within a reactor vessel. Preferably the feed slurry also contains growth medium suitable to maintain the viability of the microbial system(s) which will be used during fermentation. A viable culture of suitable microorganisms is then added to the reactor vessel to form a reaction mixture. A fermentation reaction is allowed to take place under substantially quiescent conditions while feed slurry is continuously added to the vessel as the fermentation process requires. As the reaction proceeds, there results within the reaction vessel the formation of at least three clearly defined zones. The uppermost zone in the reaction vessel is a gaseous region while the intermediate zone comprises a clarified liquid containing the produced ethanol, together with aqueous medium, microorganisms and enzymes.

The lowermost zone is the site of the fermentation reaction in which fermenting substrate (and adsorbed biocatalysts) is differentially retained within the reactor vessel with respect to fluids. The lowermost zone consists of a reaction bed, and preferably is substantially stratified such that the concentration of fermenting substrate is higher at the top of the zone than at the bottom of the zone. The actively fermenting substrate, together with adsorbed cells and enzymes, tends to be present at the upper regions of the reaction bed. As the fermentable component of the substrate is consumed during the fermentation reaction, only a rather dense, non-fermentable component remains. The insoluble substrate components are drawn by gravity to the lower regions of the reaction bed zone and collect at the bottom of the reactor vessel.

While the fermentation reaction continues, fluid from the clarified liquid zone, containing the ethanol product, aqueous medium, cells and enzymes, is continuously withdrawn from the reactor vessel and is reintroduced to the bottom of the reactor vessel. Once reintroduced, the liquid rises to the top of the vessel where the enzymes and cells become adsorbed to fresh substrate which is continuously added to the vessel. At the same time, a slurry of residue solids is withdrawn from the lower portion of stratified reaction bed.

The fluid withdrawn from the clarified liquid zone typically is separated into a stream to be reintroduced into the reactor vessel and a separate stream from which ethanol can be extracted. In a preferred embodiment, ethanol-containing fluid from the clarified liquid zone is combined with any ethanol-containing fluid withdrawn with the slurry of residue solids, and is subsequently processed to yield an ethanol product of purity sufficient for the use intended.

This configuration creates an effective internal recycling of the enzymes and cells ("biocatalysts") which facilitate the fermentation reaction, thus maintaining a high concentration of these biocatalysts within the reactor vessel due to differential substrate retention. At the same time, fermenting and fresh solid substrate levels remain high within the reactor vessel. The combination of high concentrations of substrate and biocatalysts results in an efficient fermentation process. Moreover, the ethanol production process of this invention contrasts with those typically conducted in well-mixed bioreactors which have longer reaction times and lower volumetric productivity.

DETAILED DESCRIPTION OF THE INVENTION

Figure 1:
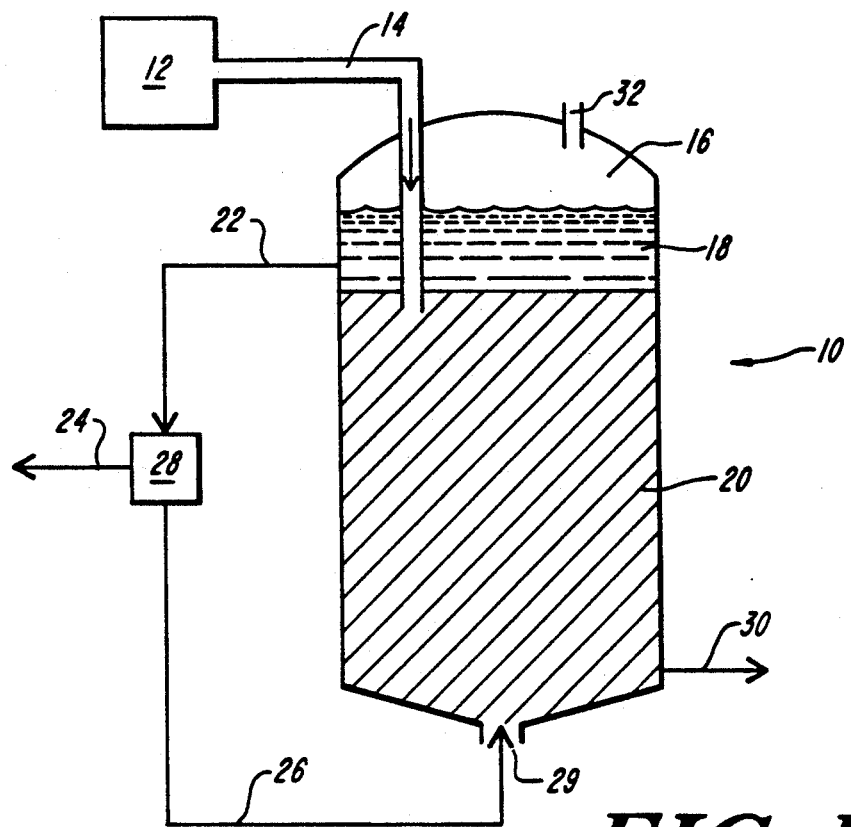
FIG. 1 is a schematic illustration of a bioreactor useful for carrying out the method of the invention.

FIG. 1 depicts a bioreactor 10 of the type useful in practicing the method of the invention. Reservoir 12 houses a slurry of lignocellulosic substrate material which is fed into bioreactor 10 through conduit 14.

During the production of ethanol in the course of carrying out the method of the present invention, at least three clearly delineated zones develop within the reactor vessel. The uppermost portion of the bioreactor forms a gaseous zone 16. Adjacent the gaseous zone is an intermediate zone 18 formed of a clarified liquid which comprises ethanol produced from the fermentation process, together with aqueous medium and biocatalysts. The lower portion of the bioreactor consists of a reaction bed zone 20 in which the fermentation reaction takes place. Preferably, the reaction bed is substantially stratified.

An additional distinct zone (not shown) may be observed within the reaction vessel, disposed between the gaseous zone 16 and the intermediate zone 18. This fourth zone comprises actively fermenting substrate particles with entrained carbon dioxide. During the fermentation process actively fermenting substrate has associated carbon dioxide which renders these substrate particles less dense than the other aqueous zones. As a result, the fermenting particles with associated carbon dioxide form a separate zone adjacent the gaseous zone.

As the reaction proceeds, clarified liquid is continuously withdrawn from intermediate zone 18 through conduit 22. The withdrawn clarified liquid comprises produced ethanol as well as aqueous medium and biocatalysts. Conduit 22 directs the withdrawn liquid to a processing and monitoring station 28 where pH is monitored and adjusted (if necessary). The liquid exits station 28 and is recirculated via conduit 26 to the bottom of the reactor through inlet 29.

Before monitoring in station 28, however, a portion of the withdrawn liquid may be diverted through conduit 24. Through subsequent processing this fluid yields an ethanol product of a desired level of purity.

Fully reacted, insoluble substrate components which collect at the bottom of the reactor vessel during the fermentation process may be withdrawn as a slurry from the bottom of the reactor vessel through conduit 30. If desired, this slurry may be separated into an insoluble, solid substrate component and an aqueous liquid component. The aqueous liquid may be combined with the effluent from conduit 24 before processing to recover ethanol.

The bioreactor also preferably contains a vent 32 from which fermentation gases may be withdrawn from the bioreactor.

The method of the invention is applicable to the production of ethanol through both the DMC and SSF process options, both of which are well known in the art. According to the method of the present invention, a reactor vessel is charged with an aqueous feed slurry of lignocellulosic substrate. A suitable amount of cellulase enzyme should be combined with the substrate if the SSF process option is utilized. A growth medium suitable for the microbial system which will be used with the process is preferably included with the feed slurry as well. Generally, the feed slurry is added such that it occupies between 80 to 90% of the reactor volume.

The reactor vessel is innoculated with a viable microbial culture (and enzyme, in the case of SSF) appropriate for the process option selected, following the addition of the feed slurry. The microbial culture is maintained in an appropriate medium under temperature and PH conditions suitable to sustain growth and to maintain viability of the culture. Although not critical, approximately 10% of the volume of the reactor vessel may be filled with the cell culture. Typically, however, the cell culture will eventually reach a steady-state concentration independent of the innoculum size.

Once the feed slurry and microbial culture are added to the reactor vessel, the system is maintained under suitable conditions to encourage fermentation. Fermentation generally commences after a period of about one to three days. Thereafter, the feed slurry is added continuously to the reactor vessel at a rate which is compatible with the growth rate of the microbial culture.

The reactor vessel is maintained in a substantially quiescent state as the fermentation reaction proceeds. As fermentation proceeds, biocatalysts become adsorbed to the solid substrate and solubilize the biodegradable component of the substrate as ethanol is produced. The reaction process produces at least three clearly delineated zones within the bioreactor. A fourth zone, as noted above, may also be formed within the bioreactor. An uppermost zone 16 is gaseous and is comprised mainly of gases produced by the fermentation process. Adjacent to and below the gaseous zone is an intermediate zone 18 which is comprised of clarified liquid. The clarified liquid comprises the ethanol product of the fermentation reaction, aqueous medium and biocatalysts. The intermediate zone 18 occupies about 10 to 40% of the reactor volume.

In some embodiments an additional, distinct zone may appear between the gaseous and intermediate zones. The fourth zone comprises actively fermenting substrate with entrained, buoyancy-imparting carbon dioxide.

The lowermost and largest zone within the reactor vessel is the reaction bed 20 which preferably occupies approximately 60 to 90% of the reactor volume. The reaction bed hosts the fermentation reaction and contains soluble and insoluble substrate, biocatalyst and aqueous medium.

During the fermentation process, the bioreactor differentially retains fermentable and fermenting substrate relative to fluid which passes through the reactor. That is, such substrates have a longer residence time within the reactor than do the fluids. This contributes to the high volumeric productivity and relatively rapid reaction rates within the reactor.

In a preferred embodiment, the reaction bed is stratified such that fermenting substrate solids with adsorbed biocatalysts tend to reside in the upper regions of the reaction bed zone since the fermentation gases associated with these materials impart some degree of buoyancy. Substrates from which the biodegradable component is partially consumed are less buoyant and tend to be drawn by gravity to intermediate regions of the reaction bed zone. Fully reacted substrate, from which only the insoluble substrate component remains, is more dense than the fluid within the reaction bed and these particulate solids settle at or near the bottom of the reactor vessel. Thus, the profile of the reaction bed is such that there is a spatially nonhomogeneous distribution of substrate where more reactive material is enriched at the top of the reaction bed zone and less reactive material is enriched at the bottom of the reaction bed zone.

In other embodiments the reaction bed may be minimally stratified such that the high concentration of reactive material at upper regions of the reaction bed and the low concentration of reactive material at lower regions is not as pronounced.

The following description is illustrative of the fermentation process of this invention. As a given particle of substrate enters the reaction bed, biocatalysts become adsorbed to the substrate and fermentation commences. During the early stages of fermentation, the reaction rate is highest and the substrate remains at or near the top of the reaction bed. Active fermentation may also occur in a separate zone which lies between the gaseous zone and the intermediate zone. As more of the biodegradable component of the substrate is consumed, the reaction rate decreases and the substrate is drawn by gravity to deeper regions of the reaction bed since its buoyancy decreases due to a decrease in associated fermentation gases, enrichment in more dense, unfermentable residue and/or convective transport of particles caused by the removal of a particulate stream at the bottom of the reaction bed. Finally, the reaction rate approaches zero as all or substantially all of the biodegradable substrate component is consumed. At this time the substrate is at or near the bottom of the reaction bed and some portion of the once-adsorbed biocatalysts become freed from the now solubilized substrate and enter the liquid phase. The freed biocatalysts move upwardly toward the region of highest fermentable substrate concentration.

While the fermentation reaction is taking place, clarified liquid is continuously withdrawn from the intermediate zone. This liquid contains aqueous medium, biocatalysts and ethanol product. Once withdrawn from the reactor, a portion of the liquid is directed through a processing station which monitors and adjusts, if necessary, the pH of the fluid. Any other necessary fluid parameters may be monitored and/or adjusted in the processing station as well. Following passage through the processing station, the withdrawn fluid is recirculated to the reaction vessel, reentering the vessel at a bottom portion hereof. The fluid reentering the vessel flows upwardly within the vessel at a rate which is less than the nominal settling velocity of the rate of particles composing the reaction bed. The portion of the withdrawn fluid which does not enter the processing station is diverted for subsequent processing to recover an ethanol product having a desired level of purity.

Figure 2:
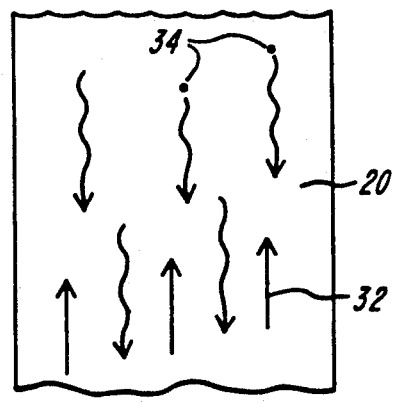
FIG. 2 is a schematic illustration of the activity within the stratified reaction bed zone of the reactor vessel.

FIG. 2 schematically illustrates conditions within the reaction bed zone during the fermentation reaction. As consumed and partially consumed substrate 34 travels downwardly within zone 20, the reintroduced fluids and associated biocatalyst (collectively indicated by arrows 32) flow upwardly within the zone. This facilitates an effective internal recycling of biocatalyst within the reaction bed zone as reintroduced and freed biocatalysts travel to the top of the reaction bed and become available for adsorption to fresh, newly added substrate. Thus, biocatalysts, like substrates, are differentially retained within the bioreactor so that high concentrations of biocatalyst and substrate are maintained at all times.

As noted, one advantage of the present method is that it allows for the differential retention of substrate, relative to fluids which pass through the reactor vessel. Since biocatalysts typically are adsorbed to substrate particles, the differential retention of substrate also allows for the differential retention of biocatalysts. The differential retention of substrate and biocatalysts helps contribute to higher reaction rates and to high volumetric productivity. Moreover, high throughput rates are maintained within the reactor vessel without "washout" which would occur with conventional bioreactors operated at the same feed residence time. Washout, which refers to the removal of biocatalysts in the effluent at a rate greater than the rate of cell growth, is undesirable because it results in loss of biocatalyst and decreased, or zero, reaction rate.

The differential substrate retention may be accompanied by the formation of a stratified substrate bed, which also increases reaction rates relative to well-mixed systems. More importantly the individual benefits of substrate and biocatalyst retention and substrate stratification are interactive in a multiplicative fashion such that a great improvement in throughput rates and reaction rates is achieved. It is believed that the system of the present invention offers a five-to-ten-fold increase over conventional, well-mixed reactor systems.

It is also surprising that a stable bed of fermenting particles is able to form in the reactor system of the present invention. Previously, it was believed that fermenting particles behave individually, without interaction between adjacent fermenting particles, and the fermentation process was thought to reduce the settling velocity of the particles causing them to be washed out of the reactor bed. However, in actively fermenting beds of pretreated hardwood substrate and *Clostridium thermocellum* formed while practicing the present invention, it has been observed that the fermenting particles tend to adhere to form macroscopic particles which, in turn, form a porous mat with improved settling characteristics. The adherence of such particles is believed to be caused by cross-linking mediated by cells and/or cellulase enzymes, and is expected to also occur in other systems which do not employ *C. thermocellum*.

A variety of microorganisms are known to be useful for the conversion of organic material to ethanol. One of ordinary skill in the art could readily select a desirable microorganism(s) for use in the method of the present invention, whether the DMC process or the SSF process options are to be used. One example of a preferred microorganism useful in converting organic matter to ethanol by way of the DMC process is *Clostridium thermocellum*. Other examples of suitable microorganisms which may be used with the DMC process option include *Fusarium oxysporum* and *C. cellulolyticum*. In addition, such organisms can be used in co-culture with *C. thermosaccharolyticum* or similar pentose-utilizing organisms such as *C. thermohydrosulfuricum* and *Thermoanaerobacter ethanolicus*.

Examples of preferred microorganisms which may be used in the practice of the method of the present invention according to the SSF technique are *Trichoderma reesei* (for producing cellulase enzyme) and *Saccharomvces cerevisiae* (which produces ethanol). Other examples of cellulase-producing organisms which may be used with the SSF process option include *Acidothermus cellulyticus* and *Trichoderma koningii*, while an alternative ethanol-producing organism which may be used with the SSF process option is *Zymomonas mobilis*. One skilled in the art can readily identify a variety of additional suitable microbial systems which may be used with the SSF process option.

A variety of suitable growth media are well known in the art and can be selected by one having ordinary skill in the art, depending upon which microorganism(s) is used. Generally, it is required that a suitable growth medium be able to provide the chemical components necessary to maintain metabolic activity and to allow cell growth. One effective growth medium contains the following components per liter of distilled water.

| | |
|---|---|
| Dilute-acid pretreated wood* | 5.0 g. |
| NaH$_2$PO$_4$ | 0.3 g. |
| K$_2$HPO$_4$ | 0.7 g. |
| (NH)$_2$SO$_4$ | 1.3 g. |
| Yeast extract | 2.0 g. |
| Morpholinopropanesulfonic acid (MOPS) buffer | 2.0 g. |
| Cysteine hydrochloride | 0.4 g. |
| MgCl$_2$.6H$_2$O | 0.2 g. |
| CaCl$_2$.6H$_2$O | 0.1 g. |
| FeSO$_4$ | 0.01 g. |

*Prepared in a plug-flow reactor at 220° C., 9 seconds residence time with 1% H$_2$SO$_4$.

The medium noted above is set forth by way of example only. It is expected that other suitable growth media may be useful for practicing the method of the invention as well.

The substrate used in practicing the method of the invention is generally categorized as a lignocellulosic raw material and is preferably Pretreated in order to render the fermentable material accessible to enzymes. Examples of such pretreatment processes include dilute-acid hydrolysis, steam explosion, and ammonia fiber explosion. Exemplary classes of lignocellulosic raw material which may be used as a substrate material include woody biomass, herbaceous biomass (e.g., forage grasses), and waste material (e.g., municipal solid waste). The size range of the substrate material varies widely and depends upon the type of material used as well as the requirements and needs of a given process. Depending on the pretreatment process employed, the size of the substrate particles, prior to pretreatment, ranges from less than a millimeter in diameter to inches in diameter. Commonly, the particle size of the substrate material after pretreatment is in the range of a few millimeters. A preferred substrate is a woody biomass material comprised of particulate hardwoods and mixtures of hardwoods. Exemplary hardwoods include poplar, oak, maple, and birch. A preferred pretreatment process for such hardwoods is dilute-acid hydrolysis.

EXAMPLE

The following example illustrates the practice of the present invention.

Pretreated mixed hardwood was autoclaved in a 20L glass carboy containing a magnetic stirring bar and a solution (Solution A) containing NaH$_2$PO$_4$, K$_2$HPO$_4$, yeast extract and MOPS buffer. A separately-autoclaved solution (Solution B) was prepared, containing cysteine hydrochloride, CACl$_2$.2H$_2$O, and FeSO$_4$. Finally, a 70% (mass basis) (NH$_4$)$_2$SO$_4$ solution was prepared and autoclaved. The A, B, and (NH$_4$)$_2$ SO$_4$ solutions were combined after sterilization in proportions of 180:3.6:1 to yield a feed slurry having the following composition

| | |
|---|---|
| Dilute-acid pretreated wood* | 5.0 g. |
| NaH$_2$PO$_4$ | 0.3 g. |
| K$_2$HPO$_4$ | 0.7 g. |
| (NH)$_2$SO$_4$ | 1.3 g. |
| Yeast extract | 2.0 g. |
| Morpholinopropanesulfonic acid (MOPS) buffer | 2.0 g. |
| Cysteine hydrochloride | 0.4 g. |
| CaCl$_2$6H$_2$O | 0.2 g. |
| CaCl$_2$6H$_2$O | 0.1 g. |
| FeSO$_4$ | 0.01 g. |

*Prepared in a plug-flow reactor at 220° C., 9 seconds residence time with 1% H$_2$SO$_4$.

The feed slurry was placed on a stir plate so that it was uniformly mixed.

A columnar fermentor with a 1.44L working volume was autoclaved separately from the feed. After autoclaving, the fermentor was filled to 25% full volume with medium prepared as above, except that AVICELL (available from FMC Corporation, Philadelphia, Pa.) replaced pretreated mixed hardwood as the fermentation substrate. Oxygen was eliminated from the system by sparging with nitrogen and also by the presence of cysteine, which acts as a reducing agent.

Withdrawal of fluid from an upper portion of the fermentor commenced prior to the addition of the microbial system. The withdrawn fluid was monitored for pH and adjusted, as necessary, with NaOH to maintain pH at about 7.0. A portion of the withdrawn fluid was reintroduced to the bottom of the fermentor while another portion was processed for ethanol extraction. This recirculation of fluid was carried out continuously throughout the process at a flow rate of 54 ml/min.

Fresh feed slurry was added to the fermentor throughout the process at a rate of 240 ml/hr. However, it is noted that this rate may be reduced to as low as 58 ml/hr.

After bringing the system to a temperature of 60° C. via circulation of heated water through the fermentor jacket, aseptic innoculation was carried out through a flame-sterilized port via a syringe. The innoculum was 50 ml of a 2-day old culture of Clostridium thermocellum (Strain ATCC 27405), grown on AVICELL in medium essentially the same as noted above, in a 160 ml crimp-seal serum bottle.

During fermentation, a stable reaction bed was formed, and substrate particles were visually observed to be retained within the system. At a 6 hour residence time, with the reaction bed occupying about 70% of the reactor column, the following solids measurements were made, verifying the existence of the reaction bed:

| Fractional height in the reactor* | Solids conc. (g/L) |
|---|---|
| 0 | 37.8 |
| 0.2 | 22.4 |
| 0.4 | 14.8 |
| 0.6 | 10.8 |
| 0.8 | 1.7 |

*Heights are measured from the bottom for a reactor with a total column height of 11.25 inches.

Throughout the fermentation process waste solids were withdrawn from the bottom of the fermentor in slurry form on an intermittent basis.

It is to be understood that various modifications can be made in the method of the invention without departing from the scope of the invention. For example, the fermentation reaction may be run using types of organisms which are not specifically disclosed herein. In addition, while the general design of a suitable bioreactor is provided herein, various modifications and refinements of the bioreactor can be made without departing from the scope of the invention.

What is claimed is:

1. A continuous process of producing ethanol from a lignocellulosic substrate, comprising the steps of:
   providing a viable, aqueous culture of microorganisms without a reactor vessel;

continuously adding to the reactor vessel a feed slurry of fermentable, lignocellulosic substrate to form a reaction mixture;

allowing the fermentation reaction to proceed while maintaining a substantially quiescent state without mechanical agitation within the reactor vessel, resulting in the formation within the reactor vessel of at least an upper, gaseous zone, an intermediate, clarified liquid zone and a lower, substantially stratified reaction bed zone in which the concentration of fermentable substrate is higher at the top of the reaction bed zone than at the bottom of the reaction bed zone;

differentially retaining fermentable substrate and adsorbed biocatalyst within the reactor vessel relative to the feed slurry during the fermentation reaction;

continuously withdrawing liquid from the intermediate zone; and extracting the ethanol product from the liquid.

2. The process of claim 1, further comprising the steps of:

accumulating insoluble, reacted substrate components at a bottom portion of the reactor vessel; and continuously withdrawing from the reactor vessel a slurry rich in the insoluble, reacted substrate components.

3. The process of claim 2 further comprising the steps of separating the withdrawn slurry into a solid substrate component and an aqueous component; and combining the aqueous component with the withdrawn liquid from the intermediate zone.

4. The process of claim 1 wherein the fermentation is conducted by Direct Microbial Conversion.

5. The process of claim 4 wherein the culture of microorganisms is selected from the group consisting of *Clostridium thermocellum, Fusarium oxysporum*, and *Clostridium cellulolyticum*.

6. The process of claim 15 wherein the culture of microorganisms is in co-culture with pentose-utilizing organisms.

7. The process of claim 1 wherein the fermentation is conducted by Simultaneous Saccharification and Fermentation.

8. The process of claim 7 wherein the culture of microorganisms is selected from the group consisting of *Trichoderma reesei, Saccharomyces cerevisiae, Acidothermus cellulolyticus, Trichoderma koningii*, and *Zymomonas mobilis*.

9. The method of claim 1 wherein the lignocellulosic substrate is wood particles.

10. The process of claim 1 wherein the lignocellulosic substrate comprises particles of mixed hardwood.

11. The process of claim 1 wherein the lignocellulosic substrate is plant matter.

12. The process of claim 1 wherein the lignocellulsic substrate is grasses.

13. The process of claim 1 wherein the lignocellulosic substrate is solid waste particles.

* * * * *

UNITED STATES PATENT AND TRADEMARK OFFICE
CERTIFICATE OF CORRECTION

PATENT NO. : 5,258,293
DATED : May 3, 1991
INVENTOR(S) : Lee R. Lynd, et al

It is certified that error appears in the above-indentified patent and that said Letters Patent is hereby corrected as shown below:

Column 1, line 18, change "utilizes," to --utilizes--.
Column 7, line 20, change "Pretreated" to --pretreated--.
Column 8, line 68, Claim 1, replace "without a reactor vessel" to --within a reactor vessel--.
Column 10, line 9, Claim 6, replace "the process of claim 15" with --the process of claim 5--.

Signed and Sealed this

Thirty-first Day of May, 1994

Attest:

BRUCE LEHMAN

*Attesting Officer*      *Commissioner of Patents and Trademarks*